(12) United States Patent
Blume

(10) Patent No.: US 7,183,237 B2
(45) Date of Patent: Feb. 27, 2007

(54) METHOD FOR THE USE OF DISTILLER'S GRAIN AS HERBICIDE AND FERTILIZER

(76) Inventor: David Blume, 534 Lattouda Dr., Aptos, CA (US) 95003

( * ) Notice: Subject to any disclaimer, the term of this patent is extended or adjusted under 35 U.S.C. 154(b) by 0 days.

(21) Appl. No.: 10/827,110

(22) Filed: Apr. 19, 2004

(65) Prior Publication Data

US 2005/0229663 A1   Oct. 20, 2005

(51) Int. Cl.
*A01N 63/02* (2006.01)
*C05F 5/00* (2006.01)
(52) U.S. Cl. .................. 504/116.1; 71/23; 47/58.1 SC
(58) Field of Classification Search ............. 504/116.1; 71/23; 47/58.1 SC
See application file for complete search history.

(56) References Cited

U.S. PATENT DOCUMENTS 2,261,923 A * 11/1941 Pittman et al. ............. 530/420
3,150,979 A * 9/1964 Ensley ....................... 424/115
3,712,802 A * 1/1973 Grybek et al ............... 504/320
5,482,529 A * 1/1996 Ahlnas et al. ................. 71/33

OTHER PUBLICATIONS

Shapiro, et al; Fertilizer Suggestions For Corn; revised Nov. 2003; 11 pages total; G74-174-A; University of Nebraska.

* cited by examiner

*Primary Examiner*—S. Mark Clardy
(74) *Attorney, Agent, or Firm*—Michael A. Guth

(57) ABSTRACT

A method of weed control using a biological paradigm. A method for the use of dried distiller's grain and soluble as an herbicide and a fertilizer in the use of crop production. A method for the processing of corn and other crops including the re-use of the dried grain by-products in subsequent crop production. A method for the production of grain alcohol including the re-use of the dried grain by-products in subsequent crop production.

16 Claims, 4 Drawing Sheets

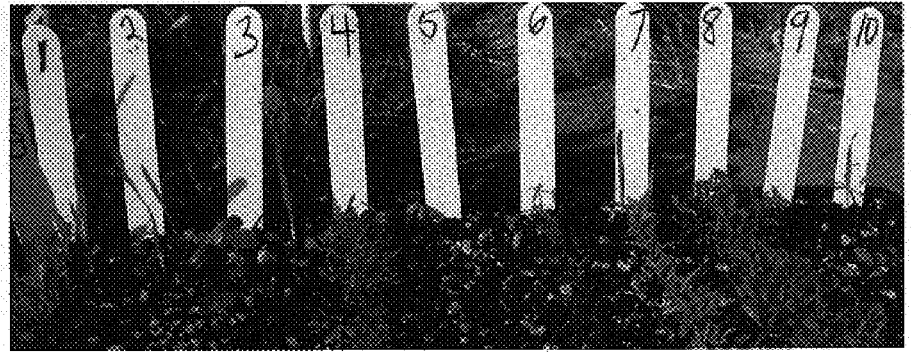
Control: All species except cocklebur #9 germinated. Germination of number 5 was weak but half a dozen plants did come up. Most of the species has robust growth even though we maintained a low temperature regime to simulate early spring conditions.

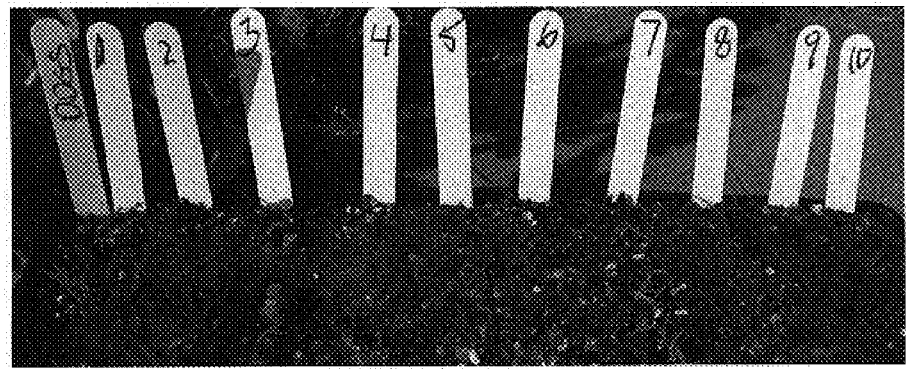
DDGS: Although several of the species did germinate, they were all inhibited either in size, number, or initiation. Several species (#2, 5, % 10) were completely prevented from germinating. DDGS results were between control and CGM and organic corn meal which sere similar.

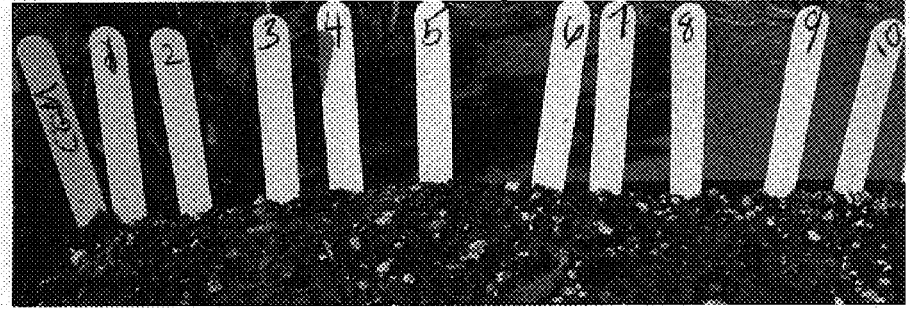
Corn Gluten Meal: Highly suppressed germination. Only 1 & 8 initially germinated. 2,4,6 came up much later (7-10) days and very weakly. Its hard to see the plants since they are so small.

FIGURE 3

METHOD FOR THE USE OF DISTILLER'S GRAIN AS HERBICIDE AND FERTILIZER

BACKGROUND

1. Field of the Invention

This invention is related to the field generally of biologically based herbicides, including the use of dried distiller's grain as an aid to plant production, and to such plant production as part of a fuel producing regime.

2. Description of Related Art

A large part of the production cost of grain has been in the control of weeds with herbicides. Weed control is implemented for a number of reasons. Greater yields of grain may occur when certain weed populations are kept low. Automated harvesting of grain is facilitated with lower interference from weeds and less debris is captured during the automatic harvesting process.

The cost of weed control may rival the net profit of the final product. The cost of herbicide application and use is a combination of bulk cost of the herbicide, labor, fuel, equipment, and other factors. Recently, genetically modified varieties of crops have been put into production which are able to tolerate direct aerial or ground application of certain herbicides. With such genetically modified varieties, the cost of weed suppression shifts from labor and fuel and instead is weighted by the costs for special seeds and seed specific chemicals. Genetically modified varieties have certain distinct drawbacks. One drawback is that often the growers cannot save their own seed without violating patent rights. Further, growers are concerned that the use of seed from a monopolized source may subject them in the future to higher costs unregulated by normal market forces. Also, genetically modified crops face significant export restrictions, and cannot be sold in high premium organic markets.

Chemically active herbicides represent a potential weed control technique. These chemical herbicides may be broken down into pre-emergent and post-emergent herbicides. Pre-emergent herbicides typically interfere with germination of weed seeds, whereas post-emergent herbicides kill the weeds after the weed seeds have germinated and weed growth has begun.

Pre-emergent herbicides may be effective when present at the required dosage at the time weed seed germination is ready to occur. However, this timing issue points out a major problem with respect to pre-emergent herbicides. Specifically, if the pre-emergent herbicide is not applied, or degrades, prior to weed seed germination, the weed seeds are free to germinate and begin growing to mature weeds. Additionally, pre-emergent herbicides are typically weed type specific and are not equally effective against all types of weeds. The timing problem present with pre-emergent herbicides may be avoided by employing post-emergent herbicides and by employing post-emergent herbicides only after the weed seeds have germinated and the weeds are actively growing. However, most available post-emergent herbicides are non-selective herbicides and will therefore kill desirable plants in addition to weeds. Except in the case of genetically modified crops, post-emergent herbicides cannot be used in proximity to crops.

Many pre- and post-emergent herbicides also suffer from another problem. Specifically, many pre-emergent and post-emergent herbicides are either moderately or highly toxic to humans and animals, and may thereby have damaging effects far beyond the intended weed control effect. Toxic herbicides may cause injury either immediately or over the long term to persons applying the herbicides and to persons present when the herbicides are applied. Also, residual concentrations of toxic herbicides that remain in the soil or water after application of the herbicide may pose a significant threat to human beings and to animals, including land-based animals and amphibians and fish, upon contact with the treated area or runoff from the treated area. Furthermore, public alarm about the use of toxic chemicals as herbicides and their potential widespread and long-term effects on environmental quality dictate against the continued use of these toxic herbicides. Use of chemical herbicides are not permitted in high value organic agriculture.

A drawback of chemically active herbicides coupled with chemical fertilizer, known as weed and feed mixtures, is that they require multiple components. In addition to the serious and harmful side effects of these chemicals, they often require separate applications, have shorter periods of action, and require specially trained personnel to apply, handle, and clean up the material. Another drawback of chemically active herbicides is that they may damage mycorhyzzal symbiotic fungi and other beneficial soil life. Chemical fertilizer may be toxic to beneficial soil organisms, for example earthworms, humus, and related organic matter. Destruction of these compounds reduces the ability of the soil to retain nutrients.

Organic vegetable growers do not use chemical herbicides or genetically modified crop varieties in their production. One of the weed control strategies used in the production of high value organic vegetables is the use of corn gluten meal. Testing by organic farmers has shown that corn gluten meal works as a pre-emergent herbicide on a wide variety of broadleaved weeds and some grasses. A pre-emergent herbicide works well for certain types of vegetable production where transplanting is the norm. The herbicidal effects of corn gluten meal seem limited to germinating seed and does not affect most transplanted crops.

The wet milling of corn produces corn gluten meal as one of its primary products. Corn gluten meal is one of many products extracted from corn during the wet milling process. A description of processes that produce corn meal is seen in U.S. Pat. No. 6,610,867 to Jakel et al. which is hereby incorporated by reference in its entirety. Other descriptions are seen in U.S. Pat. No. 6,703,227 to Jakel et al, U.S. Pat. No. 6,545,191 to Stauffer, and U.S. Pat. No. 6,509,180 to Verser which are hereby incorporated in their entireties by reference. Corn gluten meal is extracted from corn following an acid bath soaking period. Corn gluten meal may be spread on the surface of the soil after seeding or tilled in shallowly prior to seeding. The weed suppression effect of corn gluten meal continues for weeks after application. The use of corn gluten meal in this fashion is permitted for use in organic agriculture. The National Organic Standards Board (NOSB) lists corn gluten meal as a organic approved herbicide in the restricted class. However, the corn from which the corn gluten meal is derived cannot be a genetically engineered variety.

A drawback of the use of corn gluten meal as an herbicide has been its relatively high cost. Corn gluten meal has been in high demand, especially in Europe, as both chicken and cattle feed. Corn gluten meal may produce brightly colored yokes when fed to laying hens and this is a consumer preference.

SUMMARY

A method of weed control using a biological paradigm. A method for the use of dried distiller's grain and solubles as an herbicide and a fertilizer in the use of crop production. A method for the processing of corn and other crops including the re-use of the dried grain by-products in subsequent crop production. A method for the production of grain alcohol including the re-use of the dried grain by-products in subsequent crop production.

Among the many benefits of different embodiments of this invention is that it utilizes a relatively inexpensive by-product of dry-mill fuel production; can be used in conjunction with growing crops; dramatic cost production; provides weed control without the use of toxic chemicals; does not require genetic modification of the crop, does not damage beneficial soil organisms; is not subject to regulatory overburden, provides an unusually wide spectrum of nutrients; permits farmers to produce their own herbicide, fertilizer, and soil conditioner; does not kill earthworms; increases earthworm reproduction resulting in soil benefits including water infiltration, nutrient distribution, pH buffering, and solublizing nutrients; can be applied prior to transplanting in vegetable crops; increases the water holding capacity of the soil, increases soil biomass; and increases soil fertility.

BRIEF DESCRIPTION OF THE DRAWINGS

FIG. 3 is photograph illustrating a weed control trial.

DETAILED DESCRIPTION

Figure 1:
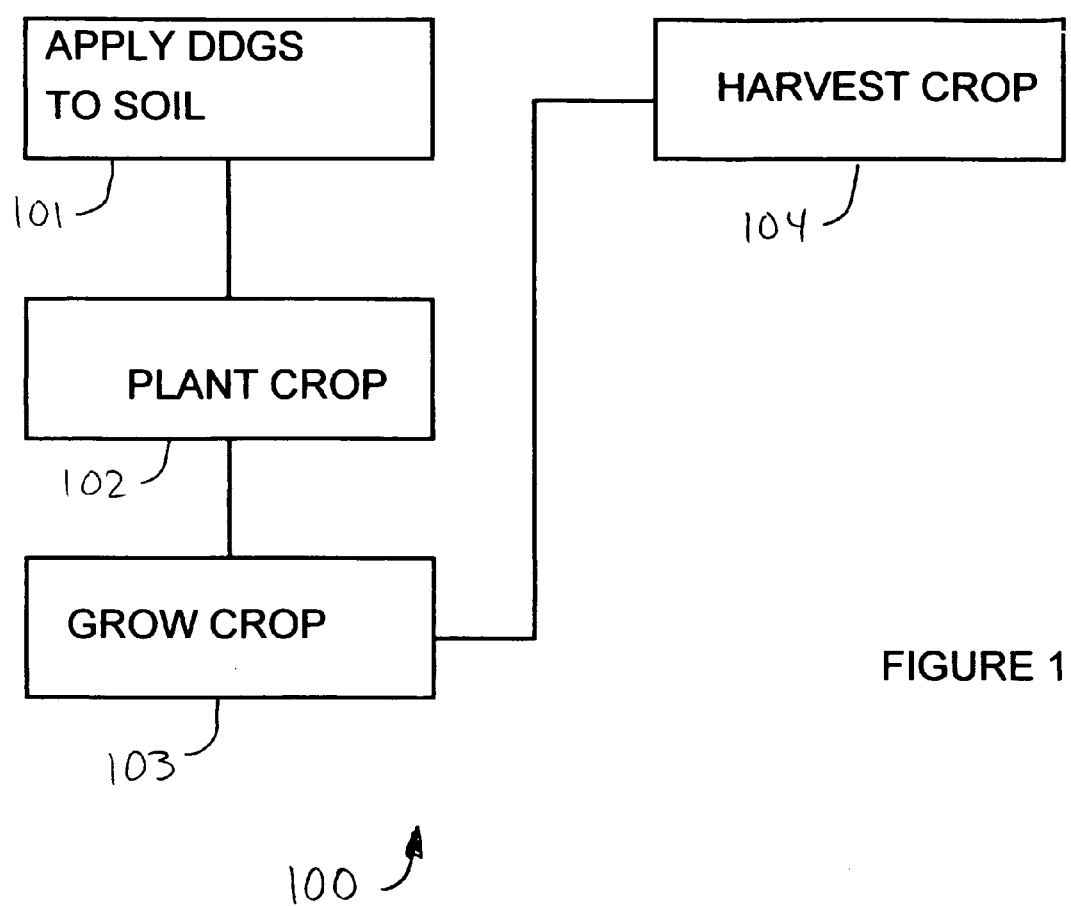
FIG. 1 is a block diagram illustrating one embodiment of the present invention.

Dried Distiller's Grain and Soluble (DDGS) is an undervalued product of dry mill alcohol fuel production. It is usually regarded as an animal feed possessing superior qualities to the dried corn from which it is made. Its higher digestibility, due to the removal of relatively indigestible flinty starch, the addition of yeast from fermentation, and other unidentified growth factors, have long been known to increase yield of meat and/or milk over straight grain feed. Alcohol fuel can be viewed as a by-product of processing grain into a superior animal feed, or DDGS can be viewed as a by-product of producing alcohol fuel.

Ethanol is a major chemical used in human beverages and food, as an industrial chemical, and as a fuel or a component in fuels, such as reformulated gasoline to reduce emissions from automobiles. There are several traditional ethanol processes based on fermentation of carbohydrates. In the most typical process, a carbohydrate derived from grain is hydrolyzed to its component sugars and fermented by yeast to produce ethanol.

DDGS may be purchased on the open market from plants that engage in the production of ethanol. DDGS is generally purchased in bulk, and may represent a mixture of by-products of different ethanol production runs. Typically, these mixtures will result in average set of chemical characteristics. These chemical characteristics have been analyzed for their fertilizer value. A typical example of some of the constituents of DDGS are as follows:

| PERCENTAGE (DDGS) | | | | | | | | |
|---|---|---|---|---|---|---|---|---|
| N | P | P2O5 | K | K2O | S | Mg | Ca | Na |
| 4.46 | 1.10 | 2.52 | 1.32 | 1.59 | .55 | .43 | .22 | .23 |

| PARTS PER MILLION (DDGS) | | | | | |
|---|---|---|---|---|---|
| Fe | Al | Mn | Cu | Zn | B |
| 1103 | 762 | 54 | 18 | 186 | 74 |

| POUNDS OF NUTRIENT/TON | | | | | | | | | | | | | |
|---|---|---|---|---|---|---|---|---|---|---|---|---|---|
| N | P | P2O5 | K | K2O | S | Mg | Ca | Na | Fe | Al | Mn | Cu | Zn | B |
| 89.2 | 22.0 | 50.4 | 26.4 | 31.8 | 11.0 | 8.6 | 4.4 | 4.6 | 2.2 | 1.5 | 0.1 | <0.1 | 0.4 | 0.1 |

An aspect of DDGS which enhances its value as an herbicide is its value as a fertilizer and a soil conditioner. DDGS is an excellent fertilizer for the very crop from which it was originally processed. DDGS may be used to provide weed control with various crops other than corn, although these would be primarily transplanted crops. DDGS also enhances water retention of the soil in part due to the cellulose content in the DDGS. The spent mash has grain and solubles in liquid suspension. The solubles in the liquid may be drained off; when none of this soluble material is returned to the grain is typically called dried distiller's grain. When the solubles are either left with the grain to dry, or returned to the grain after the liquid suspension has been removed from the dried distiller's grain, this is typically called dried distiller's grain and solubles (DDGS).

The use of DDGS in the production of a crop serves both an herbicide function and a fertilizer function. With regard to the herbicide function, DDGS may be used alone or with an active aerobic compost, earthworm castings, or other appropriate material. When applied to the soil, DDGS greatly increases the diversity and biomass of a wide variety of fungi and bacteria, as well as micro-crustaceans and other micro-fauna. Many of the fungi and bacteria are specialists at decomposition of cellulose, or generalists that can also decompose some cellulose. The fungi and bacteria undergo a population explosion when the DDGS or the combination of DDGS and active compost are applied to the soil. In a few days a massive inoculation of the fungi and bacteria dominates the soil. Corn has a large store of energy in its seed; the rate of growth of its root outstrips any biological damage. Because the DDGS is ground, condensed, seed and cellulose, the soil organisms that specialize in eating these materials are the ones which reproduce at explosive rates. Although most seeds resist the decomposing effects of these organisms by various methods in the seed coat, the DDGS is exposed and provides uninhibited feeding to the soil organisms. In areas where the soil organic matter content is below 2% the amount of soil micro-flora is reduced. In these types of areas, the mixing of fresh aerobic compost made of most any organic matter, such as vermi compost, will provide an abundance of the useful micro-flora to inoculate the DDGS and begin the rapid reproduction of soil organisms. In areas which are using this method for successive years, the addition of compost may be unnecessary after the first year.

Once the micro-organisms begin their rapid reproduction cycle, most germinating seed is attacked. Depending on the species of the germinating seed, the germinating seed is either killed or begins a battle to try to grow faster than the soil organisms can devour the growing root tips. Even if the weed survives this battle, the germinating seed has had its strength sapped and its growth is stunted. Such stunting of the growth of the weeds is often all that is necessary in crop production, as the stunted plants then become shaded by the closed canopy of the faster growing crop plants. The closure of the canopy over the weeds reduces or eliminates sunlight, and the weeds wither, die, stop growing, or have their growth slowed to a level which is not a threat to the crop plants.

Typical practical ranges for the volume per acre include 1–200 tons of DDGS per acre, depending upon soil condition, crop type, and other factors.

The drying of the DDGS is not required for this process to operate according to some embodiments of the present invention. Application of wet DDGS may provide for a faster and more vigorous action of the above-mentioned processes. Drying is typically a result of the need to dry the DDGS for economically efficient transportation of the bulk DDGS from ethanol production facilities, and for long term storage.

With regard to the fertilizer function, DDGS may have a fertilizer content which is in excess of the growing needs of the same amount of crop from which it was derived. Using nitrogen as an example, a 160 bushel per acre yield of corn is assumed to produce 4.56 tons of DDGS. At 80.87 pounds of nitrogen per ton of DDGS, 122.8 pounds of nitrogen have been produced per acre of parent crop. Using a medium nitrate level for the soil of 9 ppm, and a medium level (2%) of organic matter, the recommended amount of nitrogen to produce another 160 bushel per acre crop is 110 pounds per acre. The nitrogen in the DDGS from the parent crop is 11% more than is required to fertilize the next crop, and will push the next crop's yield to 180 bushels per acre if no other condition is limiting. In the more demanding case of a 200 bushel per acre yield, DDGS nitrogen is still in excess. In that example, 153.7 pounds of nitrogen per acre is residual in the DDGS, while the next replacement crop would only need 145 pounds of nitrogen per acre. The use of DDGS in accordance with some embodiments of the present invention builds soil fertility in succeeding years, allowing for an increase in yield. Some of the fungi are capable of piercing either the emerging root cell wall or intracellular spaces to feed on intracellular fluid. The fungi pierce the root in a symbiotic relationship. These fungi decompose and digest inorganic and organic material in the soil and pump these materials into the roots in exchange for the intracellular fluid.

Other nutrients, such as phosphorous and potassium, tend to be more insoluble and immobile, and also tend to accumulate lower in the soil below the root zone. Plants in their early growth phase may not be able to reach them. DDGS contains these nutrients both in their immediately soluble form and in their slower release insoluble mineral forms. Both forms have value. The insoluble forms are continuously chelated by fungi and bacteria to soluble forms. A typical value for the combined forms of both phosphorous and potassium from DDGS, using a 160 bushel per acre yield, are 100 pounds and 80.1 pounds respectively. The recommended amount to produce a successive crop of 160 bushels per acre is only 40 pounds of each of these constituents. Sulfur and iron are also able to be replaced at levels in excess of the requirements, as well as being provided in a proportion that is appropriate for crop production.

The application of DDGS according to some embodiments of the present invention also conditions the soil. Water retention is enhanced when DDGS is applied. This is based on a combination of at least the following: the increased biomass will absorb many times its weight in water and only slowly release it; the combination of hydrogels and the mycelia fungal mat reduce the evaporation of water; and the cellulose in the DDGS acts as a sponge holding water in the root zone.

Without being bound by any particular theory, the efficacy of the present invention may be due a combination of the above-mentioned or other factors.

FIG. 1 illustrates one embodiment of the present invention. A process 100 is used in the production of a crop. In some embodiments of the present invention, an application step 101 is used to apply the DDGS to the soil. In some embodiments, the DDGS is applied to the surface of the soil. In some embodiments, the DDGS is tilled in to the soil. After the DDGS has been applied to the soil, the crop is planted, or transplanted, as illustrated by step 102. In some embodiments, the crop is corn. In some embodiments of the present invention, the crop is planted prior to the application of the DDGS. Subsequent to the planting of the crop, the crop is grown 103. The crop is then harvested 104.

Figure 2:
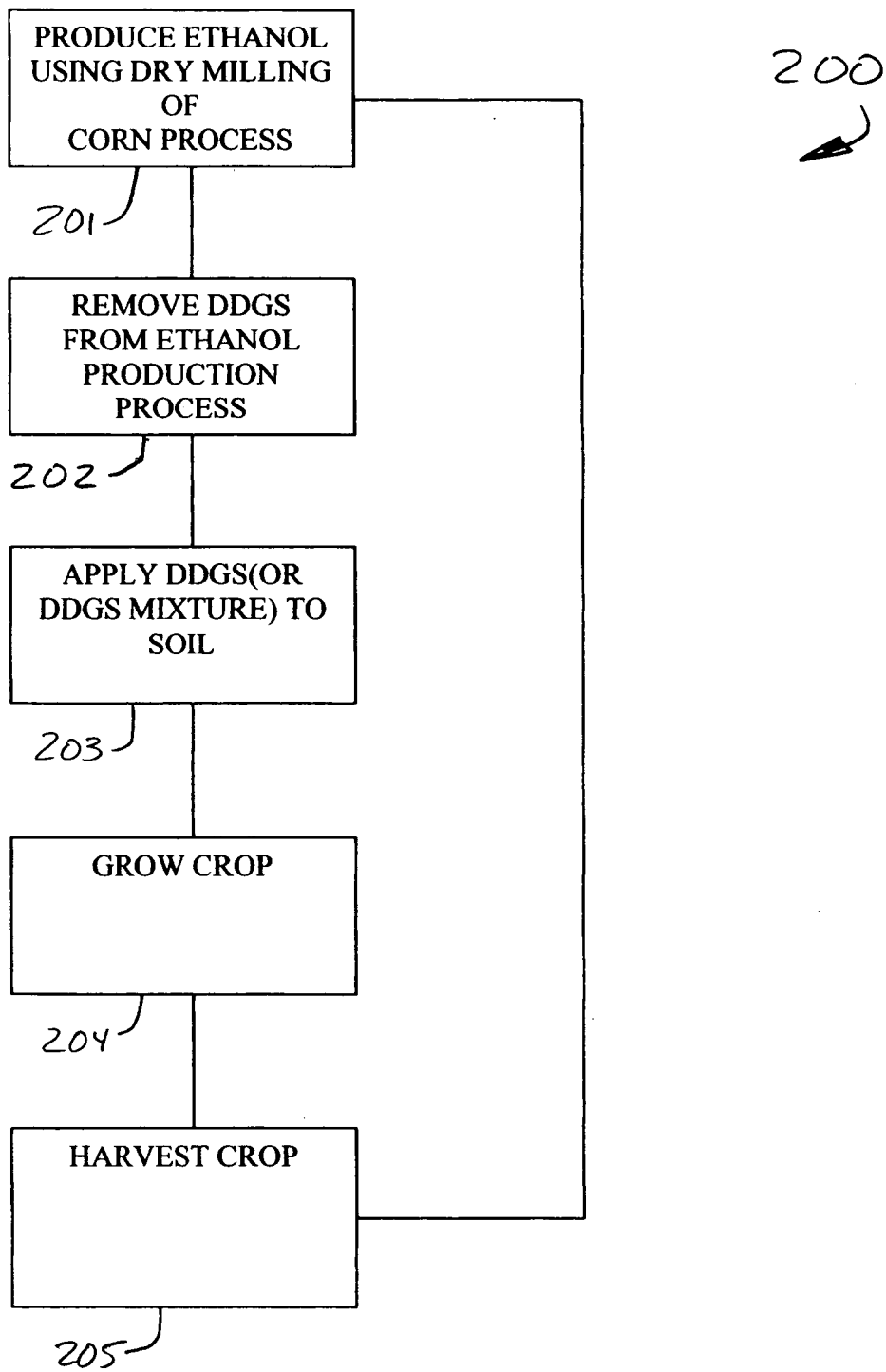
FIG. 2 is a block diagram illustrating one embodiment of the present invention.

FIG. 2 illustrates a process 20 according to one embodiment of the present invention. Ethanol or another chemical is produced using a dry milling of corn process 201. After this production of ethanol or another chemical, the DDGS is removed 202 from the previous process. In some embodiments, the DDGS is inoculated with bacteria and fungi. In some embodiments, the DDGS is inoculated with a mixture of 1% earthworm castings. DDGS is then applied to soil that is to be used for the growing of a crop such as corn 203. The crop is then grown 204, and then harvested 205. In some embodiments of the present invention, this crop is then used to produce ethanol or another chemical, thus completing a cycle. In some embodiments of the present invention, the amount of DDGS produced allows for coverage of more soil than in the previous cycle, allowing for expansion of the crop's growing area, or an increase in fertility in the same or lesser area. In some embodiments of the present invention, the soil in a subsequent cycle is not the same soil, or is not in the same geographic vicinity, as the soil in the previous cycle.

Trials

In one weed control trial, several square, 2.5 inch deep flats filled with commercial potting mix were used as the base to substitute for soil. Organic substrate potting mix was used because it more closely approximates loamy soil than most mixes which use a large percentage of synthetic ingredients. The potting mix nutrients are largely supplied by compost and earthworm castings and the potting mix is not enriched with chemical fertilizers. No fertilizer was applied in this trial.

The purpose of this trial was to test for the herbicidal effects of various compounds against common weeds. Ten of the most common weeds in corn agriculture were used in this trial. It is expected that this collection should be the most adapted to corn and the most resistant to any herbicidal effect due to natural selection. The 10 weeds selected were: (1) green foxtail, (2) fall panicum, (3) velvetleaf, (4) water hemp, (5) giant ragweed, (6) lamb's quarters, (7) barnyard grass, (8) red pigweed (*amaranth* sp), (9) cockleburr, and (10) smart weed. The numbers associated with the weeds above are referred to again in the trial results section. In each flat 10 rows were opened to an approximate depth of ⅜ inches. One weed species was planted per row. Four flats were configured this way.

The potting mix in flat 1 was covered by 10 ounces of corn gluten meal. Flat 2 was covered by 10 ounces of DDGS. Flat 3 was covered by 10 ounces of organic corn meal (OCM). Flat 4 was used as a control and no material was used. For this trial the material was simply added to the surface.

OCM was used for two reasons. The first was to rule out the possibility of herbicidal action by the CGM being a result of residual chemical herbicide from the source grain. Because OCM is free of chemical herbicide, the use of OCM acts as a control against the contamination of CGM. The second reason was to check if corn itself was herbicidal, based on the theory that allopathic diffusion approximating a natural action by corn to reduce competition to its own germinating offspring was at play.

In this trial, the planted flats were initially covered at night. The flats were exposed during the day to partial sunlight to simulate cool spring soil conditions typical of the natural germination phase. The covering was discontinued after 10 days into the trial. The covering used was sheet cardboard; sheet cardboard would not "seal" the soil and thus no anaerobic effects would occur as a result of the covering.

The flats were irrigated daily for the first twenty days to simulate approximately one half of one inch of rain per day. Because this trial involved surface application of the materials to the planting area, the applied level of irrigation precluded any significant drying and thus was also simulative of the conditions when the material added to the planting area would be tilled into the soil. Moist soil is indicative of the condition when crops are germinating. A typical moisture value is 23%.

A second trial was conducted simultaneously to test for the possibility of herbicidal effects of DDGS on corn itself. Since corn is usually not a transplanted crop, herbicidal effects that would affect the germination of corn would not be welcome. In this second trial, flats were prepared in which corn seed was planted in excess of one half of one inch deep. The same compounds were used as in the weed control trial, except for that 20 ounces of compound per flat were used. The increased amount was used because it was believed that the herbicidal effect against corn would be low, and the increased amount would allow a better possibility of observable results. The same irrigation and covering regimes were used as in the weed control trial. Typical values used are seen in Fertilizer Suggestions for Corn, G74-174-A, by Shapiro et al., September 2001, University of Nebraska, Lincoln.

Trials Observations

Weed control trials—FIG. 3 is photograph illustrating a weed control trial. Selected observations:

Day 1: All 3 materials readily wetted and individual flakes and grits expanded visibly.

Day 2: Visual observation that on all three materials extensive fungal and bacterial growth had been initiated. No fungal growth was observed on the control flat. Both filamentous fungi and single celled bacteria flourished on the surface. Expansion of the particles continued.

Day 3: Visual observation that the growth of the fungi and bacteria were producing what appeared to be various hydrogels and the filamentous fungi had knitted together in a fairly homogenous fashion by the end of the day. Visual observation of filaments as long as 1.5 cm in length.

Day 4: The biological mat was responding to irrigation by initially soaking up water and then sealing the surface to ready absorption in many places. Water would then sit up to an hour before soaking in. Lactic acid bacteria were detected.

Days 5–10: Largely stabilized top surface with continued water conserving characteristics and slow infiltration times. Modest water erosion of soil surface on the control flat arrested completely on fungal flats. Filamentous fungi visibly dying back especially where exposed to greater direct sunlight, but still very present below ground extending at least 2 cm from the surface.

Figure 4:
FIG. 4 is a photograph illustrating a corn trial.

Germination: (Illustrative photographs are seen in FIG. 4)

Day 11: Pigweed (8) broke ground in the control flat.

Day 12: Green foxtail (1), Fall panicum (2), Velvetleaf (3), and Lamb's quarters (6) all broke ground strongly in the control flat.

Day 13: Velvetleaf (3) and Pigweed (8) thinly germinated in the CGM flat. A few Pigweed (8) germinated on the DDGS flat.

By the end of the week (day 18) all varieties except Cockleburr (9) had germinated strongly in the control flat and were doing well. No variety was doing well in the OCM, DDGS, and CGM flats a week later The flat with the most apparent weed suppression was the OCM flat. It had the least number of species germinating, the least number of individuals in a given row, and the least growth in the seedlings that did come up. In the CGM flat, only weed types 1 and 8 came up initially, with 2, 4, and 6 coming up 7–10 days later than in the control group. In the DDGS flat, weed types 2, 5, and 10 were all completely suppressed and did not germinate. All other weed species were severely stunted, or delayed, compared to the control flat and exhibited a low percentage of germination.

Effect on Corn Trial

Observations: All corn seed germinated in all flats. There was a one day delay in germination time and initial growth in the OCM flat. In the control, DDGS, and CGM flats initial growth was similar with the OCM flat experiencing slower growth. Later, and especially following the fourth week, significantly faster growth and substantially greater biomass accumulation occurred in the OCM, CGM, and DDGS flats. By the sixth week it became clear that the DDGS seedlings were as much as double the biomass of the control flat, and significantly greater in biomass than the CGM and OCM flats. The deepness of the green color of the corn, indicating nitrogen adequacy, was most developed in the DDGS flat, followed by the CGM flat. FIG. 4 is a photograph illustrating a corn trial.

In some embodiments of the present invention, different grains are used. In some embodiments of the present invention, DDGS is applied while wet. In some embodiments of the present invention, DDGS may be inoculated with cultivated strains of microorganisms. In some embodiments of the present invention, DDGS may be applied at more than one time during the growing cycle.

As evident from the above description, a wide variety of embodiments may be configured from the description given herein and additional advantages and modifications will readily occur to those skilled in the art. The invention in its broader aspects is, therefore, not limited to the specific details and illustrative examples shown and described. Accordingly, departures from such details may be made without departing from the spirit or scope of the applicant's general invention.

I claim:

1. A method for the growing of crops comprising applying dried distiller's grain and soluble (DDGS) to the soil in which the crops are to be grown.

2. The method of claim 1 wherein said crops comprise corn.

3. The method of claim 1 wherein said applying DDGS to the soil comprises tilling said DDGS into the soil prior to seed of said crops.

4. The method of claim 1 wherein said applying DDGS to the soil comprises spreading said DDGS onto the top surface of the soil.

5. The method of claim 4 wherein between 1 and 200 tons of DDGS are spread on each acre of planting area.

6. The method of claim 3 wherein between 1 and 200 tons of DDGS are tilled into each acre of planting area.

7. A method comprising
processing corn, wherein said processing corn yields dried distiller's grain and soluble (DDGS) as a by-product, and
applying said DDGS to the soil in which corn is to be grown.

8. The method of claim 7 wherein said applying DDGS to the soil comprises spreading said DDGS onto the top surface of the soil.

9. The method of claim 7 wherein said applying DDGS to the soil comprises tilling said DDGS into the soil prior to seeding.

10. The method of claim 7 further comprising growing corn in said soil.

11. A method for the growing of crops comprising applying a mixture of organic compost dried distiller's grain and soluble (DDGS) to the soil in which the crops are to be grown.

12. The method of claim 11 wherein said crops comprise corn.

13. The method of claim 11 wherein said applying a mixture of organic compost and DDGS to the soil comprises tilling said mixture of organic compost and DDGS into the soil prior to seeding of said crops.

14. The method of claim 11 wherein said applying a mixture of organic compost and DDGS to the soil comprises spreading said mixture of organic compost and DDGS onto the top surface of the soil.

15. The method of claim 1 further comprising planting corn into said soil.

16. The method of claim 1 further comprising transplanting a crop into said soil.

* * * * *